United States Patent [19]

Haining

[11] Patent Number: 5,533,983
[45] Date of Patent: Jul. 9, 1996

[54] VALVED MEDICAL CONNECTOR

[76] Inventor: Michael L. Haining, 6731 Ashmore, Houston, Tex. 77069

[21] Appl. No.: 350,418

[22] Filed: Dec. 6, 1994

Related U.S. Application Data

[63] Continuation-in-part of Ser. No. 218,380, Mar. 28, 1994, abandoned, which is a continuation-in-part of Ser. No. 157,306, Nov. 25, 1993, Pat. No. 5,401,245.

[51] Int. Cl.⁶ ............................ A61M 5/00; A61M 25/00; F16K 51/00
[52] U.S. Cl. ..................... 604/249; 604/283; 251/149.1
[58] Field of Search .................... 604/82, 83, 86, 604/88–91, 246, 249, 280, 283, 284, 905, 167, 169; 251/149.1, 149.3, 149.6, 149.7

[56] References Cited

U.S. PATENT DOCUMENTS

| | | |
|---|---|---|
| 1,692,047 | 11/1928 | Moore . |
| 3,812,841 | 3/1974 | Isaacson . |
| 4,361,147 | 11/1982 | Aslanian et al. . |
| 4,436,125 | 3/1984 | Blenkush . |
| 4,506,691 | 3/1985 | Tseo . |
| 4,629,159 | 12/1986 | Wellenstam . |
| 4,683,916 | 8/1987 | Raines . |
| 4,699,356 | 10/1987 | Hargrove et al. . |
| 4,745,950 | 5/1988 | Mathieu . |
| 4,790,832 | 12/1988 | Lopez ........................................ 604/283 |
| 4,957,483 | 9/1990 | Gonser et al. . |
| 5,041,087 | 8/1991 | Loo et al. . |
| 5,049,128 | 9/1991 | Duquette . |
| 5,131,429 | 7/1992 | Nixon . |
| 5,163,922 | 11/1992 | McElveen et al. . |
| 5,184,652 | 2/1993 | Fan . |
| 5,199,947 | 4/1993 | Lopez et al. . |
| 5,273,254 | 11/1993 | McNaughton et al. . |
| 5,277,402 | 1/1994 | Szabo . |
| 5,297,776 | 3/1994 | Dieringer ............................ 251/149.1 |

FOREIGN PATENT DOCUMENTS

906563  2/1982  U.S.S.R. .

Primary Examiner—John D. Yasko
Assistant Examiner—Adam J. Cermak
Attorney, Agent, or Firm—Richard L. Moseley

[57] ABSTRACT

A needleless connector for adding medication to a parenteral fluid is provided. In one embodiment an adapter is provided for securing to a Y connector having a standard puncture pad. The adapter includes a cannula for piercing the pad and a valve that is opened by the attachment of a syringe. In a second embodiment the Y connector itself contains the valve in lieu of the puncture pad. In a final embodiment the valve is contained within a universal luer connector adapter.

3 Claims, 7 Drawing Sheets

VALVED MEDICAL CONNECTOR

This application is a continuation-in-part of my earlier application Ser. No. 08/218,380 filed Mar. 28, 1994 (now abandoned), which was a continuation-in-part of application Ser. No. 08/157,306 filed Nov. 25, 1993, now U.S. Pat. No. 5,401,245.

BACKGROUND OF THE INVENTION

1. Field of the Invention

This invention relates to medical connectors used in the introduction of liquids into patients via intravenous solutions. More particularly the invention relates to a needleless connection for use with syringes or other apparatus having a standard luer lock type connection.

2. Related Information

It is a common practice in treating patients, particularly patients who must be cared for under emergency conditions, using medications introduced into the patient intravenously. An intravenous solution, commonly referred to as parenteral fluid, is fed from a container or I.V. bag through a tubing and a catheter which has been inserted into the patient's vein. The catheter is secured to the patient by a strip of adhesive tape. The medication to be administered is generally added to the parenteral fluid through a Y connector in the tubing. The conventional practice has been to inject the fluid using a hypodermic syringe and needle through a sealed entry port in Y connector in the tubing. Generally the seal at the port is a puncture pad of generic latex which for a limited number of uses will reseal itself when a needle is withdrawn.

One problem with this conventional practice is that the needle may be pulled loose from the sealed port very easily. Another problem is needle sticks. From time to time a nurse in attempting to insert the needle into the port will accidentally stick himself or herself with the needle. While there is little risk of infection to the nurse if the needle is new and sterile, the process may be slowed until the needle has been replaced. Lopez, et al in U.S. Pat. No. 4,752,292 have presented one solution to the problem.

The connector of Lopez, et al presumes that the needle connector may be easily attached to the source of medication. When measured doses are necessary syringes are more often used and the Lopez connector is not practical.

It is an object of the present invention to provide a needleless connector for administering medication through a Y connector of an I.V. system.

SUMMARY OF THE INVENTION

In its simplest form the present invention comprises a connector adapted to receive a syringe and having a valve to seal the port in place of a puncture pad. The valve comprises a stem with a plug on one end. The stem is biased by a spring such that the plug is normally seated. When a syringe or other apparatus having a male luer connection is engaged with the connector the stem is depressed opening the valve allowing the medication to flow through the connector into the tubing and thus to the patient. The invention may be described as a connector for adding a fluid to a intravenous solution, comprising:

(a) a valve housing having a seat at one end;

(b) a valve stem slidably mounted within said housing having a plug on one adapted to sealably fit into said seat;

(c) a spring mounted about said stem to bias said plug against said seat thereby closing said valve; and (d) an actuator means on said stem at the end opposite said plug for moving said stem against said spring bias to move said plug away from said seat thereby opening said valve.

Another variation is use of the valve in a universal connector having a male luer connection on one end and a female luer connection on the other. This embodiment allows for use of the valve adaptor for any standard luer connection.

DESCRIPTION OF THE PREFERRED EMBODIMENT

For a detailed description of the preferred embodiment the reader is directed to the accompanying figures in which like components are given like numerals for ease of reference.

Figures 1, 2:
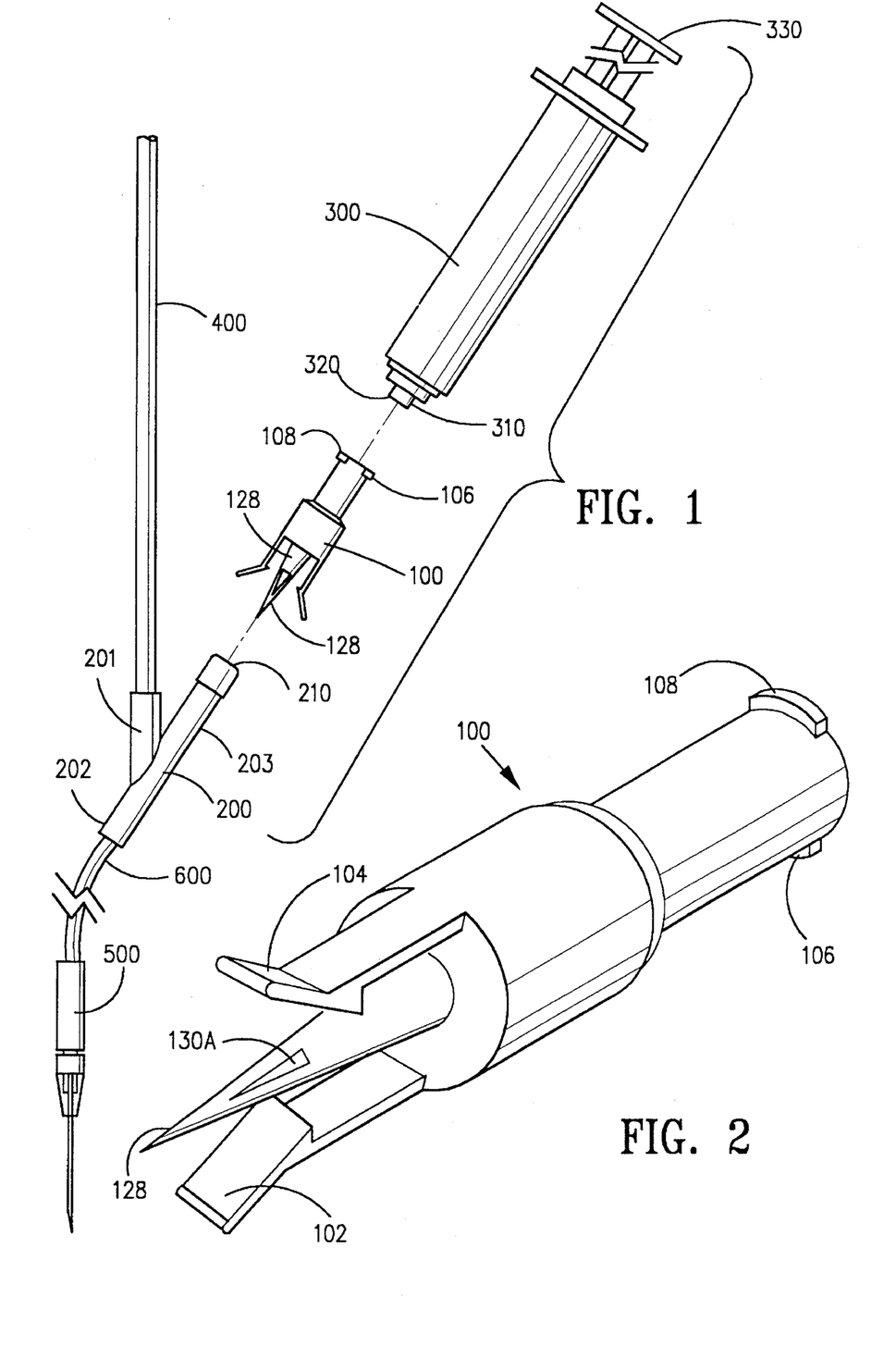
FIG. 1 is a schematic view of a conventional I.V. system and an adapter connector of the present invention and a syringe.
FIG. 2 is a perspective view of an adapter connector utilizing the valve of the present invention.
Figure 3:
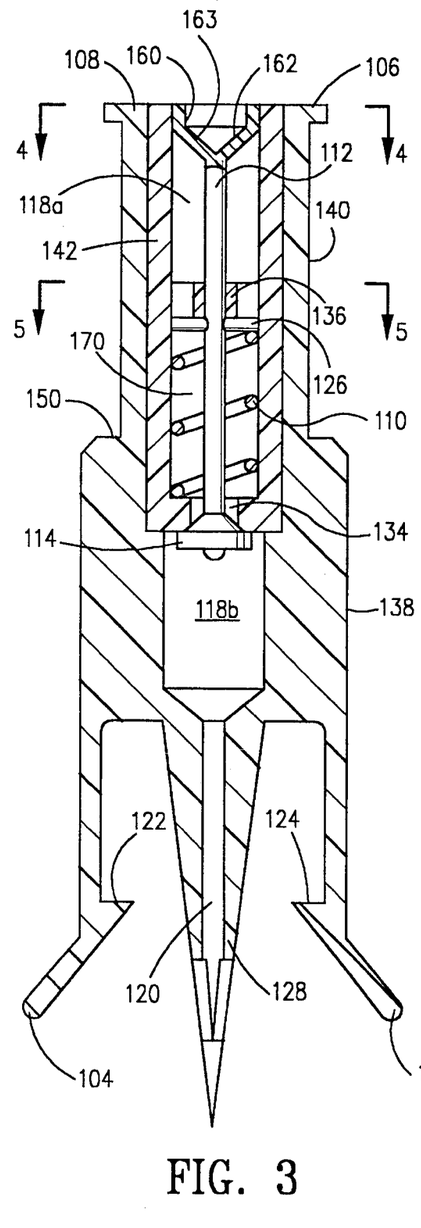
FIG. 3 is a plan view in cross section of the adapter connector of FIG. 2.
Figure 4:
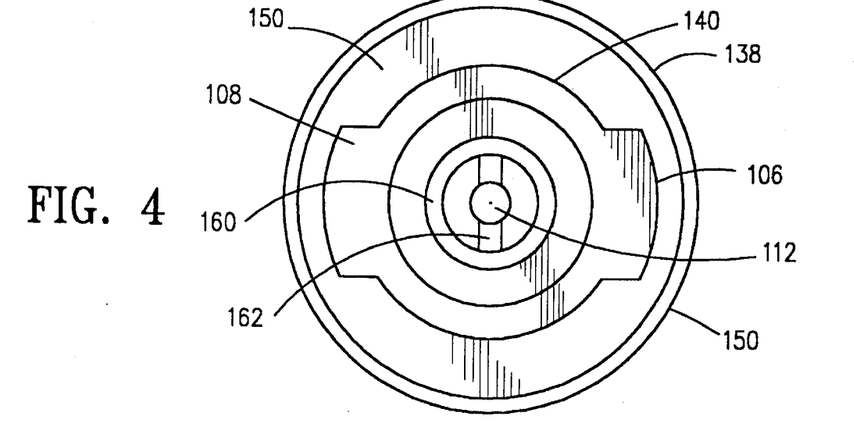
FIG. 4 is a top view of the adapter connector of FIG. 2.
Figure 5:
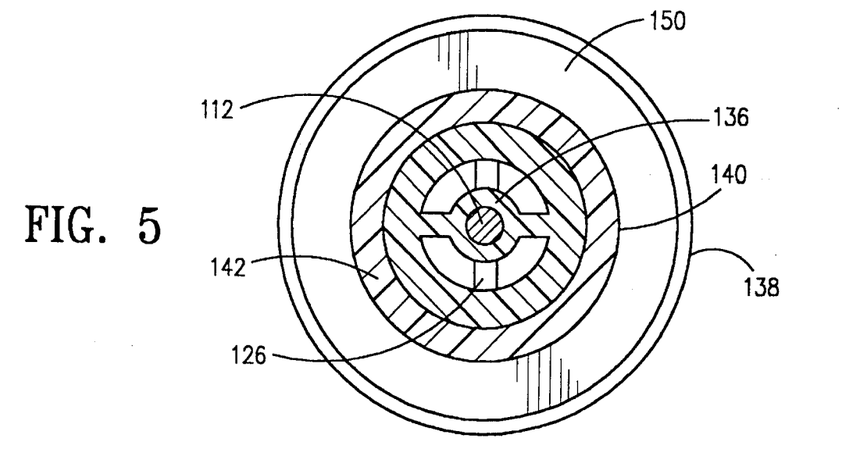
FIG. 5 is a view of the adapter connector taken along line 5—5 in FIG. 3.
Figure 6:
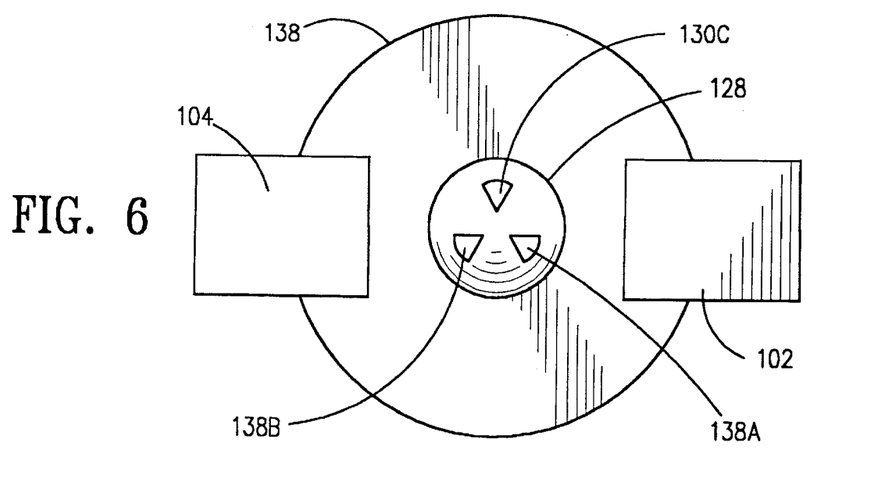
FIG. 6 is a bottom view of the adapter connector of FIG. 2.

Referring first to FIG. 1 there is shown an intravenous fluid administration system. A first tube 400 is attached by one end to a source of parenteral solution (not shown) and by the 3 opposite end to a Y connector 200. A second tube 600 is connected at a first end to the lower end of the Y connector and at the lower end is connected to an intravenous catheter 500. Since the fluid is administrated by gravity flow the direction up, down, upper and lower have definite meanings.

The Y connector is shown to have three connection points or ports. The first port 203 is for receiving the medication which is injected from a syringe 300 and should be angle up from the horizontal to allow injected fluid to flow by gravity into the Y connector and tube 600. The second port 202 is connected to the catheter tube 600. The third connection port 201 is for connection to the parenteral fluid tube 600. The first port 203 extends at an angle from the Y connector 200 such that it is less than 90° from the vertical or from the third port 201. First port 203 is sealed by a puncture pad 210 which in normal systems is pierced by a hypodermic needle mounted on a syringe. In one embodiment of the present invention a connector adapter 100 is provided which includes a cannula 128 which pierces the puncture pad 210. Connector adapter also includes standard luer connections 106 and 108 for normal threaded engagement with the syringe. Additionally, as shown in FIG. 2 the connector adapter includes flexible wings 102 and 104 which may engage and lock about the puncture pad. Once the connector adapter 100 is installed there is no need to use a hypodermic needle with the syringe and thus the risk of accidental needle prick is reduced.

The puncture pad normally provides for a resealable access to the Y connector. To replace the function of the puncture pad a valve is provided within the connector 100, the details of which are shown in FIGS. 3–7. Referring now to FIGS. 3–6 the adapter connector 100 with the valve contained therein is shown. The adapter connector is seen to have a body having two axially aligned cylindrical barrels— larger diameter barrel 138 and smaller barrel 140 which are connected by shoulder 150. Extending from the lower end are two flexible wings 102 and 104 each having internal surfaces 122 and 124 respectively for engagement with the puncture pad (not shown in FIGS. 3–6). Extending centrally from the lower body 138 is cannula 128.

The upper end of the connector adapter 100 is shown to have standard luer connections 106 and 108 which engage the luer threads 310 of syringe 300. As shown the syringe 300 includes the standard plunger 330 for injecting the fluid through the adapter connector 100 into the Y connector 200.

Internally the body is seen to have two axially aligned cylindrical cavities—upper cavity 118a which is of larger diameter than lower cavity 118b. A channel 120 is provided through cannula which allows for fluid passage from lower cavity 118b and out cannula openings 130a, 130b and 130c.

As depicted the valve is shown to be a separate entity which may be assembled first and then inserted into upper body cavity 118a. The valve includes a cylindrical housing 142 which fits snugly into upper cavity 118a and is secured there by an appropriate cement, A lower opening 134 in the valve allows fluid communication to lower cavity 118b when the valve is opened, If desired the housing may be have external threads which may engage internal threads of upper cavity 118a. The threaded engagement is not shown, Inside the housing 142 the valve is seen to include a stem 112 which has a plug at the lower end, A spring 110 is mounted about the stem 112 and held in place between the bottom of the valve housing and a horizontal bar 126 secured to stem 112, Upward movement of the stem is limited by the plug which seats on the underside of the valve housing, The spring 110 provides an upward bias force to keep the plug 114 seated and the valve closed. Stem guide 136 is provided for stability of movement along the axis of the valve.

The stem 112 is connected to a "dough nut" actuator 160 at the upper end by two support rods 162 and 163, The upper surface of the "dough nut" actuator is flush with the upper surface of the valve housing which in turn is flush with the upper surface of the upper body barrel. The top of the connector adapter is thus even for ease of cleaning.

Figure 7:
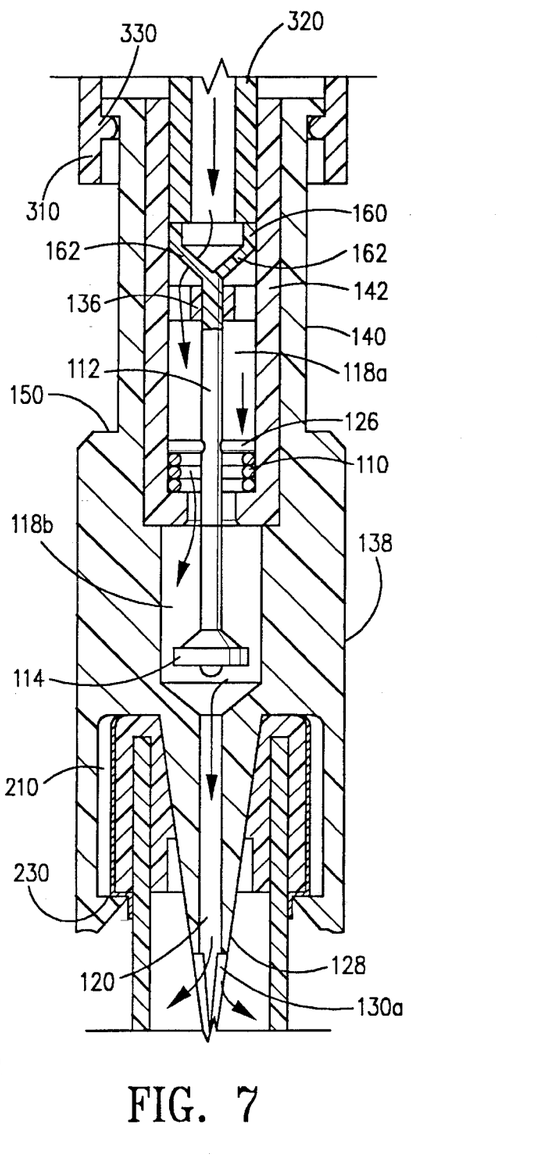
FIG. 7 is a plan view in cross section of the adapter connector of FIG. 2 with a syringe attached and the valve open.

Referring now to FIG. 7 the connector adapter 100 is shown attached to Y connector 200, Cannula 128 is passed through puncture pad 210 and surfaces 122 and 124 have engaged surfaces 230 of puncture pad to secure the connector adapter to the Y connector 200, Threads 330 in syringe engage the luer connection 106 and 108 on upper end of connector adapter and extension 320 on syringe is forced downward against the "dough nut" actuator which in turn forces stem 112 downward to unseat plug 114 and open valve into lower cavity 118b. The flow of fluid may be followed by the arrows.

Figures 8, 9:
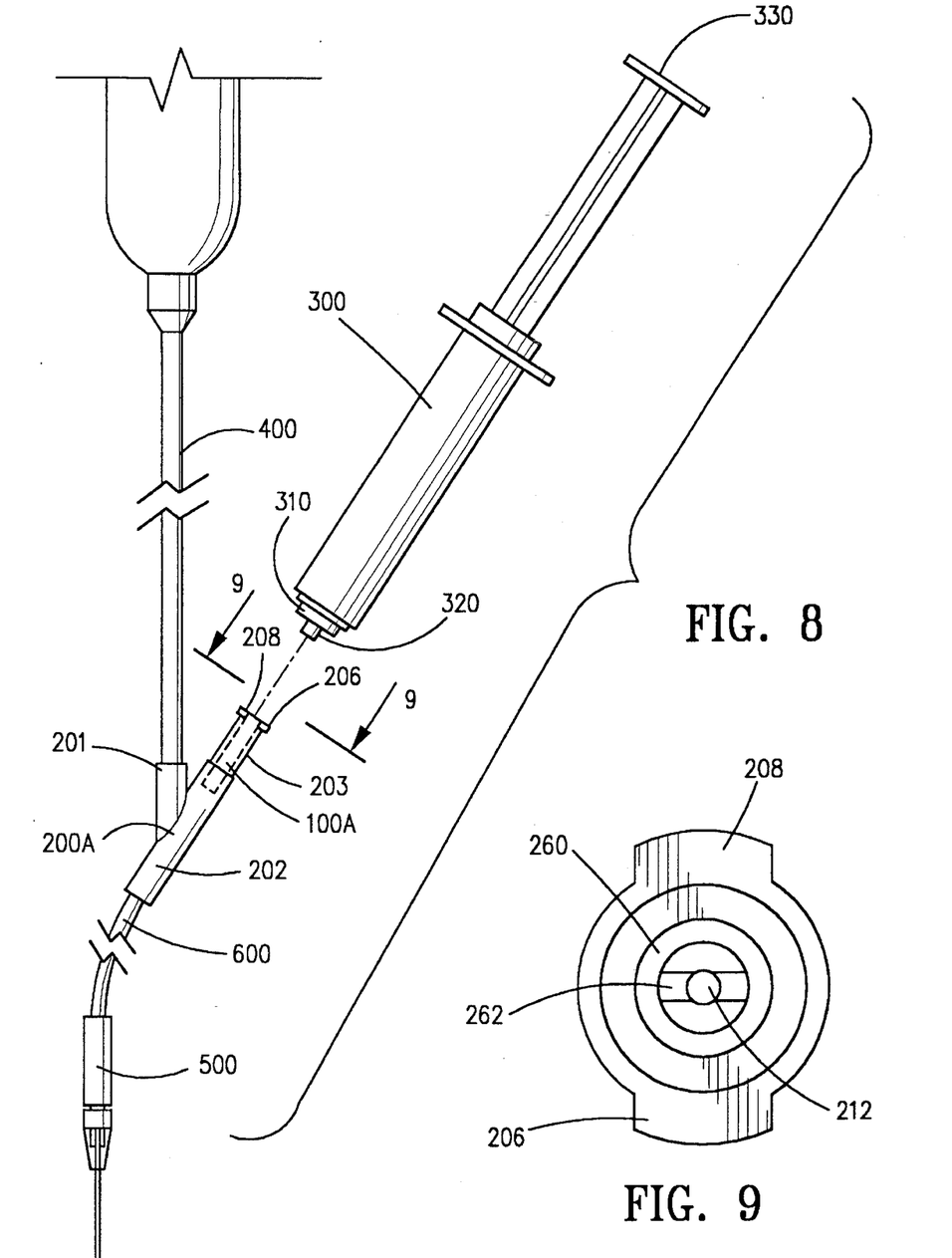
FIG. 8 is a schematic of an I.V. system with the valve of the present invention included in the Y connector.
FIG. 9 is a view of the Y connector of taken along line 9—9 in FIG. 8.

In a second embodiment the valve is placed directly into the first port of the Y connector. This intravenous fluid administration system is shown in FIG. 8. As in the previous embodiment there is shown an intravenous supply tube 400 connected to port 201 of Y connector 200A. A second tube 600 is connected to second port 202 of Y connector and to catheter 500. The first port 203 is provided for administering the medication into the parenteral fluid. As in the previous Y connector the first port 203 extends at an angle from the Y connector 200 such that it is less than 90° from the vertical or from the third port 201. The first port 203 is for receiving the medication which is injected from a syringe 300 and should be angle up from the horizontal to allow injected fluid to flow by gravity into the Y connector and tube 600. Instead of the puncture pad the valve 100a is provided. At the end of the first 203 port are luer connections 206 and 208 which may be threadedly engaged with the luer connection of the syringe 300 having plunger 330 for injecting the fluid into the Y connector.

Figure 10:
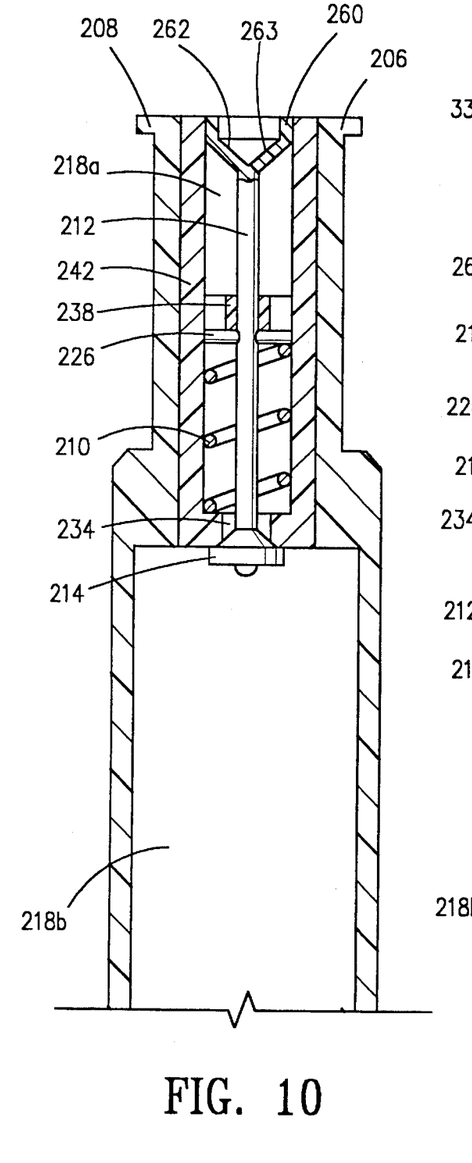
FIG. 10 is a plan view in cross section of the valve within the Y connector of FIG. 8.

Referring now to FIGS. 9 and 10 the construction of the port 203 containing the valve 100a is shown. The details of the valve assembly is the same as in the adapter connector. The valve includes a cylindrical housing 242 which fits snugly into upper cavity 218a and is secured there by an appropriate cement. A lower opening 234 in the valve allows fluid communication to lower cavity 218b when the valve is opened If desired the housing may be have external threads which may engage internal threads of upper cavity 218a. The threaded engagement is not shown.

Inside the housing 242 the valve is seen to include a stem 212 which has a plug 214 at the lower end. A spring 210 is mounted about the stem 212 and held in place by the bottom of the valve housing and a horizontal bar 226 secured to stem 212. Upward movement of the stem is limited by the plug which seats on the underside of the valve housing. The spring 210 provides an upward bias force to keep the plug 214 seated and the valve closed. Stem guide 236 is provided for stability of movement along the axis of the valve.

The stem 212 is connected to a "dough nut" actuator 260 at the upper end by two support rods 262 and 263. The upper surface of the "dough nut" actuator is flush with the upper surface of the valve housing which in turn is flush with the upper surface of the upper body barrel. The top of the port is thus even for ease of cleaning.

Figure 11:
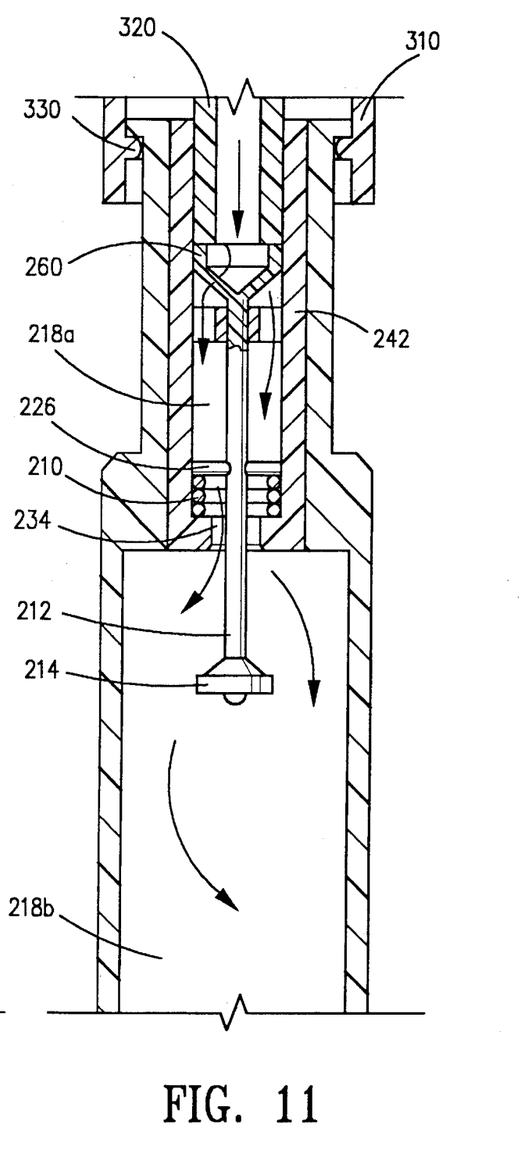
FIG. 11 is a plan view in cross section of the valve in the Y connector of FIG. 10 with a syringe attached and the valve open.

Referring now to FIG. 11 the syringe 300 is shown connected to the port 203 of Y connector 200. Threads 330 in syringe engage the luer connection 206 and 208 on upper end of connector adapter and extension 320 on syringe is forced downward against the "dough nut" actuator which in turn forces stem 212 downward to unseat plug 214 and open valve into lower cavity 218b. The flow of fluid may be followed by the arrows.

Figure 12:
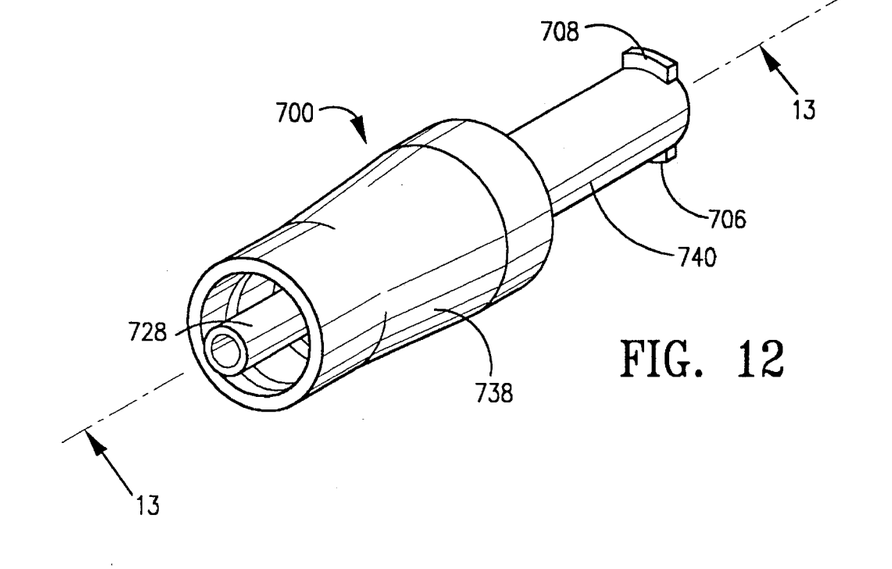
FIG. 12 is an isometric view of a universal tubing connector utilizing the valve of the present invention.
Figure 13:
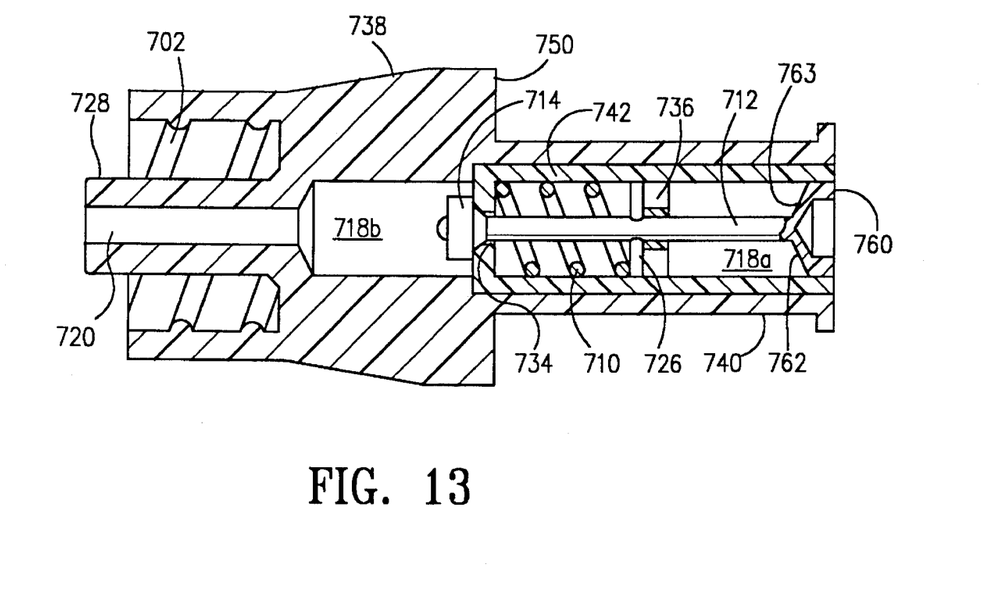
FIG. 13 is a plan view in cross section on the tubing connector of FIG. 12 taken along line 13—13.

Referring now to FIGS. 12 and 13 the universal adapter connector 700 with the valve contained therein is shown. The adapter connector is seen to have a body having two axially aligned barrels—larger diameter tapered barrel 738 and smaller cylindrical barrel 740 which are connected by shoulder 750. Extending centrally from inside the lower body 738 is cylindrical extension 728. Internally of the lower body 738 are standard threads 702 which may engage any standard male luer connection.

The upper end of the connector adapter 700 is shown to have standard luer connections 706 and 708 which may be used to engage any standard female luer connection as on a syringe.

Internally the body is seen to have two axially aligned cylindrical cavities—upper cavity 718a which is of larger diameter than lower cavity 718b. A channel 720 is provided through cylindrical extension 728 which allows for fluid passage from lower cavity 718b and out of the connector adapter.

As depicted the valve is shown to be a separate entity which may be assembled first and then inserted into upper body cavity 718a. The valve includes a cylindrical housing 742 which fits snugly into upper cavity 718b and is secured there by an appropriate cement. A lower opening 734 in the valve allows fluid communication to lower cavity 718b when the valve is opened If desired the housing may be have external threads which may engage internal threads of upper cavity 718a. The threaded engagement is not shown.

Inside the housing 742 the valve is seen to include a stem 712 which has a plug at the lower end. A spring 710 is mounted about the stem 712 and held in place by the bottom of the valve housing and a horizontal bar 726 secured to stem 712. Upward movement of the stem is limited by the plug which seats on the underside of the valve housing. The spring 710 provides an upward bias force to keep the plug 714 seated and the valve closed. Stem guide 736 is provided for stability of movement along the axis of the valve.

The stem 712 is connected to a "dough nut" actuator 760 at the upper end by two support rods 762 and 763. The upper surface of the "dough nut" actuator is flush with the upper surface of the valve housing which in turn is flush with the upper surface of the upper body barrel. The top of the connector adapter is thus even for ease of cleaning.

Figure 14:
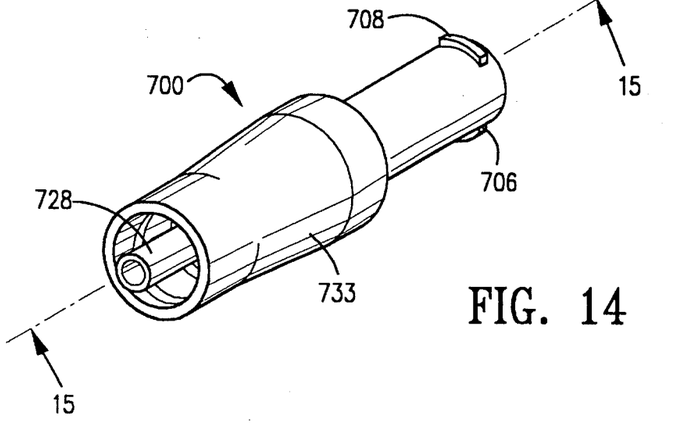
FIG. 14 is an isometric view of a second embodiment of a universal tubing connector utilizing the valve of the present invention.
Figure 15:
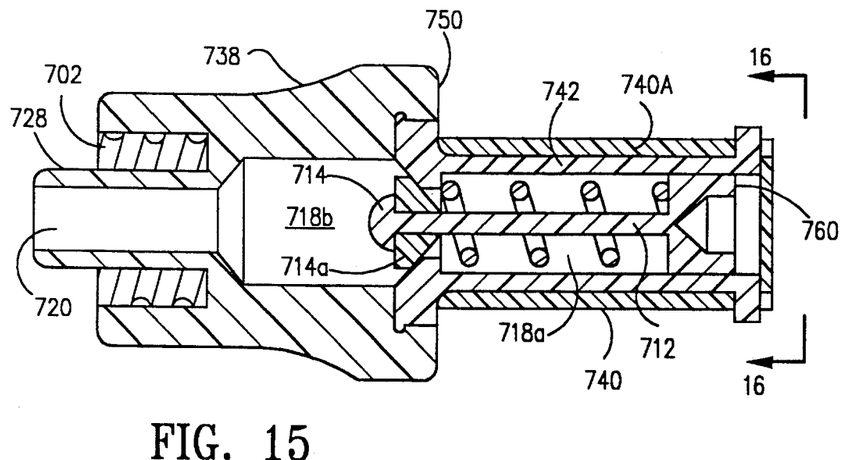
FIG. 15 is a plan view in cross section of the tubing connector of FIG. 14 taken along line 15—15.
Figure 16:
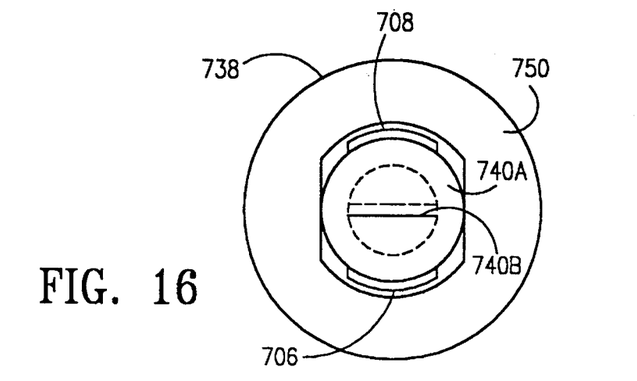
FIG. 16 is a top plan view of the tubing connector of FIG. 15 taken along line 16—16.

Finally FIGS. 14–16 depict a second embodiment of the universal tubing connector is shown. The connector is essentially the same as that shown in FIGS. 12 and 13 except that a rubber cover 740A is provided over the barrel 740 and the end of the barrel. A pre-cut slit 740B is provided in the rubber cover 740A over the end of the barrel for insertion the luer connector. The remaining reference numeral are the same as in FIGS. 12 and 13.

The connector adapter is designed to be used with existing Y connectors while the second embodiment is preferred with the valve being integrated within the Y connector. The third connector adapter is designed to be used with any luer connection. In addition, the rubber cover shown in FIGS. 14–16 may be placed over the luer receiving end of any of the connectors shown in the figures.

The invention claimed is:

1. A medical connector comprising:

(a) a cylindrical body having an upper cavity and a lower cavity, said upper cavity having a valve seat at one end;

(b) a valve stem slidably mounted within said upper cavity having a plug on one end adapted to sealably fit into said seat;

(d) a spring mounted about said stem to bias said plug against said seat thereby closing said valve;

(e) an actuator means on said stem at the end opposite said plug for moving said stem against said spring bias to move said plug away from said seat thereby opening said valve;

(f) a cylindrical extension axially mounted on the lower end of said body defining an annular space between the outer surface of said extension and the inner surface of said lower cavity;

(g) internal threads on the inner surface of said lower cavity for engagement with a male luer connector; and (h) a rubber cover over said upper body covering said actuator means.

2. The medical connector of claim 1 further comprising a male luer connection on the upper end of said body for engagement with a female luer connector.

3. The medical connector of claim 1 further comprising a slit in said rubber cover directly over said actuator means.

* * * * *